United States Patent
Hedlund et al.

(10) Patent No.: US 11,896,564 B2
(45) Date of Patent: Feb. 13, 2024

(54) MEDICAL TREATMENT FOR PATHOLOGIC INFLAMMATION

(71) Applicant: PHARMACYL AB, Bjärred (SE)

(72) Inventors: Gunnar Hedlund, Lund (SE); Anders Björk, Bjärred (SE)

(73) Assignee: PHARMACYL AB, Bjärred (SE)

( * ) Notice: Subject to any disclaimer, the term of this patent is extended or adjusted under 35 U.S.C. 154(b) by 540 days.

(21) Appl. No.: 17/264,924

(22) PCT Filed: Aug. 15, 2019

(86) PCT No.: PCT/EP2019/071903
§ 371 (c)(1),
(2) Date: Feb. 1, 2021

(87) PCT Pub. No.: WO2020/035554
PCT Pub. Date: Feb. 20, 2020

(65) Prior Publication Data
US 2022/0087959 A1 Mar. 24, 2022

(30) Foreign Application Priority Data
Aug. 15, 2018 (EP) .................................... 18189194

(51) Int. Cl.
*A61K 31/166* (2006.01)
*A61P 1/04* (2006.01)
*A61K 45/06* (2006.01)

(52) U.S. Cl.
CPC ............ *A61K 31/166* (2013.01); *A61K 45/06* (2013.01); *A61P 1/04* (2018.01)

(58) Field of Classification Search
CPC .... A61K 31/166; A61K 45/06; A61K 31/196; A61K 31/655; A61K 31/167; A61K 31/606; A61K 31/635; A61K 2300/00; A61P 1/04; A61P 19/02; A61P 29/00; A61P 37/06; A61P 1/00; C07C 237/34; C07C 237/30
See application file for complete search history.

(56) References Cited

U.S. PATENT DOCUMENTS

| | | | |
|---|---|---|---|
| 3,177,252 A | 4/1965 | Thominet | |
| 6,100,299 A | 8/2000 | Pero | |
| 6,518,312 B2 | 2/2003 | Bjork et al. | |
| 2011/0027179 A1 | 2/2011 | Friebe et al. | |

FOREIGN PATENT DOCUMENTS

| | | |
|---|---|---|
| EP | 0 927 030 B1 | 7/1997 |
| EP | 1720531 B1 | 4/2011 |
| WO | 99/63987 | 12/1999 |
| WO | 2005025498 A2 | 3/2005 |
| WO | 2018037103 A1 | 3/2018 |

OTHER PUBLICATIONS

Pero, Ronald W. et al., "Multiple Mechanisms of Action of the Benzamides and Nicotinamides as Sensitizers of Radiotherapy: Opportunities for Drug Design," Cancer Detection and Prevention, 22(3):225-236 (1998).
Amidon, et al. "Colon-Targeted Oral Drug Delivery Systems: Design Trends and Approaches," AAPS PharmSciTech; vol. 16, No. 4; Aug. 2015.
Khan, et al.; "An Experiment to Determine Theactive Therapeutic Moiety of Sulphasalazine;" The Lancet; pp. 892-895; Oct. 29, 1977.
Harrington, et al.; "Metoclopramide: An Updated Review of its Pharmacological Properties Clinical Use;" Philadelphia College of Pharmacy and Science, Philadelphia, and ADIS Drug Information Services, Auckland and New York; pp. 451-194; 1983.
Harron, et al.; "Acecainide (N-Acetylprocainamide): A Review of its Pharmacodynamic and Pharmacokinetic Properties, and Therapeutic Potential in Cardiac Arrhythmias;" The Queen's University of Belfast, Belfast, Northern Ireland, and ADIS Drug Information Services, Auckland, New Zealand; pp. 720-740; 1990.
S. B. Hanauer; "Review article: aminosalicylates in inflammatory bowel disease;" Aliment Pharmacol Ther; vol. 20, Suppl. 4, pp. 60-65; 2004.
Ivanenkov, et al.; "Small Molecule Inhibitors of NF-KB and JAK/STAT Signal Transduction Pathways as Promising Anti-Inflammatory Therapeutics;" Mini-Reviews in Medicinal Chemistry; vol. 11, pp. 55-78; 2011.
Kim, et al.; "5-Aminosalicylic Acid Azo-Linked to Procainamide Acts as an Anticolitic Mutual Prodrug via Additive Inhibition of Nuclear Factor kappaB;" Molecular Pharmaceuticals; pp. 2126-2135; Apr. 26, 2016.
Jung, et al.; "Synthesis and Properties of Dextran-5-aminosalicylic Acid Ester as a Potential Colon-specific Prodrug of 5-Aminosalicylic Acid;" Archives of Pharmaceutical Research; vol. 21, No. 2, pp. 179-186; 1998.

(Continued)

*Primary Examiner* — Deborah D Carr
(74) *Attorney, Agent, or Firm* — Renner, Otto, Boisselle & Sklar, LLP

(57) ABSTRACT

A compound of formula (I) or a pharmaceutically acceptable salt or solvate thereof, for use in combination with a 5-ASA agent, in the treatment of a disease resulting from pathologic inflammation. The combination of a compound of formula (I) or a pharmaceutically acceptable salt or solvate thereof and 5-ASA agent and use of such combination. A kit-of-parts and a pharmaceutical composition comprising such a combination.

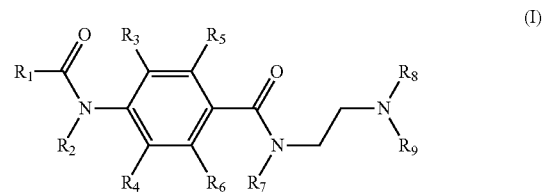

(I)

23 Claims, No Drawings

(56) References Cited

OTHER PUBLICATIONS

Jung, et al.; "Synthesis and Properties of 5-Aminosalicyl-taurine as a Colon-specific Prodrug of 5-Aminosalicylic Acid;" Archives of Pharmaceutical Research; vol. 26, No. 4, pp. 264-269; 2003.

Yan, et al.; "Aminosalicylic Acid Inhibits IκB Kinase α Phosphorylation of IκBα in Mouse Intestinal Epithelial Cells*;" Gastroenterology; pp. 602-609; Mar. 1999.

Liberg, et al.; "N-substituted benzamides inhibit NFkB activation and induce apoptosis by separate mechanisms;" British Journal of Cancer; pp. 981-988; 1999.

Lim, et al.; "Aminosalicylates for induction of remission or response in Crohn's disease (Review);" Cochrane Database of Systematic Reviews; Issue 7; 2016.

Lindgren, et al.; "Differential usage of IjBa and IjBb in regulation of apoptosis versus gene expression," Biochemical and Biophysical Research Communications; pp. 204-211; 2003.

Lindgren, et al; "N-substituted benzamides inhibit nuclear factor-KB and nuclear factor of activated T cells activity while inducing activator protein 1 activity in T lymphocytes;" Molecular Immunology; pp. 267-277; 2001.

MacDermott, et al.; "Progress in Understanding the Mechanisms of Action of 5-Aminosalylic Acid;" The American Journal of Gastroenterology; vol. 95, No. 12; 2000.

Mills, et al.; "Colonic Crohn's Disease;" Clinics in Colon and Rectal Surgery; vol. 20, No. 4, pp. 309-313; 2007.

Peppercorn, et al.; "The Role of Intestinal Bacteria in the Metabolism of Salicylazosulfapyridine;" The Journal of Pharmacology and Experimental Therapeutics; vol. 181, No. 3., pp. 555-562; 1972.

Pero, et al.; "Newly discovered anti-inflammatory properties of the benzamides and nicotinamides;" Molecular and Cellular Biochemistry; pp. 119-125; 1999.

Perse, et al.; "Dextran Sodium Sulphate Colitis Mouse Model: Traps and Tricks;" Journal of Biomedicine and Biotechnology; vol. 2012, 13 pages; Mar. 5, 2012.

Rang, et al.; "New molecules in analgesia;" British Journal of Anaesthesia; pp. 145-456; 1995.

Svartz; "Salazopyrin, a new sulfanilamide preparation.;" Acta Medica Scandinavica; vol. CX; 1942.

Thompson, et al.; "IKB-p Regulates the Persistent Response in a Biphasic Activation of NF-KB;" Cell; vol. 80, pp. 573-582; Feb. 24, 1995.

Van Hees, et al.; "Effect of sulphapyridine, 5-aminosalicylic acid, and placebo in patients with idiopathic proctitis: a study to determine the active therapeutic moiety of sulphasalazine;" Gut; pp. 632-635; 1980.

Wahl et al.; "Sulfasalazine: a Potent and Specific Inhibitor of Nuclear Factor Kappa B;" American Society for Clinical Investigation, Inc.; vol. 101, No. 5; Mar. 1998.

Wang, et al.; "Oral 5-aminosalicylic acid for maintenance of remission in ulcerative colitis (Review);" Cochrane Database of Systematic Reviews; Issue 5; 2016.

Wang, et al.; "Oral 5-aminosalicylic acid for induction of remission in ulcerative colitis (Review);" Cochrane Database of Systematic Reviews; Issue 4; 2016.

Zhao, et al.; "Amelioration of Dextran Sulfate Sodium-induced Chronic Colitis by Sulfasalazine Salicylazosulfapyridine via Reducing NF-kB Transcription Factor p65 Recruitment to ICAM-1 Gene Promotors;" The Pharmaceutical Society of Japan; vol. 130; May 18, 2010.

International Search Report for corresponding international application PCT/EP2019/071903 dated Nov. 8, 2019.

International Preliminary Report on Patentability for corresponding international application PCT/EP2019/071903 dated Feb. 2, 2020.

Aihara, et al. "Salazosulfapyridine and 5-aminosalicylic acid agents" Japanese Clinical Journal, 1999, vol. 57, No. 11, pp. 2476-2480, with English abstract.

MEDICAL TREATMENT FOR PATHOLOGIC INFLAMMATION

This application is a national phase of International Application No. PCT/EP2019/071903 filed Aug. 15, 2019 and published in the English language, which claims priority to European Application No. 18189194.6 filed Aug. 15, 2018, both of which are hereby incorporated herein by reference.

FIELD OF THE INVENTION

The present invention relates to compounds for use in the treatment of diseases resulting from pathologic inflammation. More particularly, the invention relates to 4-alkanoylaminobenzamide derivatives for use in combination with 5-aminosalicylate (5-ASA) agents in the treatment of inflammatory bowel disease (IBD). Furthermore, the invention relates to combinations of 4-alkanoylaminobenzamide derivatives and 5-ASA agents and to pharmaceutical formulations and kit-of-parts comprising such combinations.

BACKGROUND OF THE INVENTION

Throughout this application, various (non-patent) publications are referred to by first author and year of publication. Full citations for these publications are presented in a References section immediately before the claims. The disclosures of these documents and publications referred to herein are hereby incorporated in their entireties by reference into this application in order to more fully describe the state of the art to which this invention pertains.

Inflammatory Bowel Diseases (IBD)

IBD, mainly comprised of Crohn's disease (CD) and ulcerative colitis (UC), is a chronic, frequently progressive condition of the gastrointestinal tract that requires lifelong treatment. The natural history of this condition is one of periods of remission, punctuated by relapses of disease activity. CD and UC are diseases with many similarities, but differ frequently with respect to localization and how they are managed. UC is characterised by relapsing and remitting mucosal inflammation starting in the rectum, extending to proximal segments of the colon and characterised histologically by the presence of both acute and chronic inflammation. The diagnosis of UC is based on a combination of symptoms, endoscopic findings, and histology. The pathogenesis is multifactorial, involving genetic predisposition, dysregulated immune responses, and environmental factors. CD can involve any portion of the gastrointestinal system. Approximately 60% of patients with CD suffer from colonic involvement. Half of those patients have the disease limited to the colon (Mills, 2007).

Depending on the extent of disease, UC patients can be classified as having 1) ulcerative proctitis involving only the rectum, 2) left sided UC involving the colorectum distal to the splenic flexure and 3) extensive UC involving the colon proximal to the splenic flexure (includes pancolitis). Symptoms may vary depending on the degree and extent of inflammation. Patients are classified as having mild, moderate or severe disease activity according to one or more measures of disease severity. The hallmark symptom of UC is bloody diarrhoea accompanied by urgency to defecate. Other symptoms include crampy abdominal pain, loss of appetite, fatigue, weight loss and fevers. Traditionally, the highest occurrence of both CD and UC is found in the developed countries of North America and Europe. The prevalence is estimated to be 70-500 cases per 100.000, with males and females affected equally. People are more frequently diagnosed for UC between the ages of 15 and 35, and at a second lesser peak between 55 and 65 years of age. The median age at diagnosis is 30 years. In 15% of cases UC is diagnosed in childhood and may present before school age. CD and UC account for substantial costs to the health care system and society.

UC has a substantial impact on the patient's quality of life due to early onset and lack of a cure. Current medications are moderately efficacious, and adverse effects are a problem. It is therefore urgent to improve clinical management by establishing new treatment strategies. The therapeutic goals are induction and maintenance of remission and prevention of complications. Patients with mucosal healing who have no or very mild signs and symptoms are considered in remission. The ultimate treatment goal for all patients with UC is steroid-free clinical and endoscopic remission. Effect on the inflammatory process is essential since lack of control of inflammation even in the presence of control of symptoms is correlated with poor long term outcome. The risk of colectomy and colorectal cancer is increased in patients who fail to respond to medical management. Extra-intestinal manifestations of UC include primary sclerosing cholangitis, as well as joint, skin and eye manifestations.

Treatment of IBD

Therapeutic recommendations depend on the disease location, disease severity, and disease complications. First-line therapy in mild to moderate UC includes administration of the 5-aminosalicylate (5-ASA; mesalazine [CAS No. 89-57-6]) agents. Sulfasalazine (SASP [CAS No. 599-79-1]), an azo-bonded prodrug of 5-ASA, is the parent 5-ASA agent. SASP provides a modest benefit for the treatment of mild to moderately active CD (Lim, 2016). Patients who are failing or do not respond fully to 5-ASA drugs can be treated with corticosteroids or immunomodulators (thiopurines). Tumour necrosis factor-alpha (TNFα) blockers are indicated for the treatment of UC patients with moderately to severely active UC, and who have failed conventional therapies. Serious side effects, however, limit the use of these types of drugs. Clearly, there is an obvious need for new drugs with higher efficacy and safety for induction and then maintenance of clinical and endoscopic remission.

5-ASA in UC

The mainstay of therapy for mild to moderate UC is 5-ASA agents (Hanauer, 2004). The successful management of UC was greatly facilitated after the introduction of SASP (Svartz 1942). It is generally considered that 5-ASA represents the therapeutically active moiety of SASP (Azad Khan 1977; van Hees 1980). Orally ingested SASP is enzymatically split in the colon into 5-ASA and sulfapyridine (CAS No. 144-83-2) (Peppercorn 1972), thus releasing 5-ASA acting locally on the colonic mucosa. Other azo-bonded 5-ASA agents include olsalazine (CAS No. 15722-48-2) and balsalazide (CAS No. 80573-04-2). Other 5-ASA delivery systems use for example pH-dependent delayed-release formulations to liberate the 5-ASA in sufficient concentrations directly in the colon (Amidon 2015). Both oral and rectal therapies are effective in inducing and maintaining remission. Once daily is the optimal dosing and there is marginal evidence for a significant dose-response effect above 2400 mg/day.

Systematic reviews and meta-analyses of patients with active mild to moderate UC comparing 5-ASA to placebo showed 5-ASA significantly superior to placebo (Wang 2016a; Wang 2016b). Seventy-one percent of 5-ASA patients failed to enter clinical remission compared to 83% of placebo patients. 5-ASA was also found superior to placebo for maintenance therapy. Forty-one percent of 5-ASA patients relapsed compared to 58% of placebo patients. No statistically significant differences in efficacy were found between 5-ASA and SASP for induction of remission (Wang 2016a). SASP, however, was found significantly superior to 5-ASA for maintenance of remission (Wang 2016b).

5-ASA Mechanism of Action

The mechanism of action exerted by 5-ASA agents remains unclear, but a central mechanism that explains the inhibitory effects of 5-ASA on multiple pathways of inflammation may be due to its inhibition of nuclear factor kappa B (NFκB) activation (MacDermott, 2000). SASP has been shown to be a potent inhibitor of NFκB activation, able to suppress NFκB dependent transcription, and able to prevent nuclear translocation of NFκB due to inhibition of inhibitory κBα (IκBα) phosphorylation and subsequent degradation (Wahl, 1998; Zhao, 2010). 5-ASA has been demonstrated to inhibit TNFα stimulated NFκB activation, NFκB nuclear translocation, and degradation of IκBα (Kaiser, 1999).

Activation of NFκB

NFκB is considered to be a heterodimer of proteins that belong to the Rel family of transcription factors (TF). A common feature of the regulation of TFs belonging to the Rel family is their sequestration in the cytoplasm as inactive complexes with a class of inhibitory molecules known as IκBs. Treatment of cells with different inducers, e.g., TNFα, results in the dissociation of the cytoplasmic complexes and translocation of free NFκB to the nucleus. There are two major biochemically characterized forms of IκB proteins in mammalian cells, IκBα and IκBβ. The primary difference between IκBα and IκBβ is in their response to different inducers of NFκB activity. One class of inducers causes rapid but transient activation of NFκB by primarily affecting IκBα complexes, whereas another class of inducers causes persistent activation of NFκB by affecting both IκBα and IκBβ complexes. Therefore, the overall activation of NFκB consists of two overlapping phases, a transient phase mediated through IκBα and a persistent phase mediated through IκBβ. The distinct behaviour of the two IκBs following stimulation fulfils the promise of differential regulation suggested by the existence of multiple IκB isoforms. Although the two major IκB isoforms interact with the same Rel proteins, they are activated by distinct signaling pathways, probably eliciting very different physiological responses. While the IκBα response is used for responding immediately to transient situations of stress, the persistent response through IκBβ may be utilized for situations of chronic inflammation, infection, stress, or differentiation (Thompson, 1995).

4-Aminobenzamides

The 4-aminobenzamides including metoclopramide (CAS No. 364-62-5) and procainamide (CAS No. 51-06-9) constitute a class of compounds that have been developed for a number of clinical indications and screened or used as antiemetics, antiarrhythmics, local anaesthetics, antiinflammatory agents, antitumor agents and radio/chemosensitizers (Stanley, 1982; Rang, 1995; Pero, 1998 and 1999). The diverse clinical applications of these drugs are paralleled by equally diverse mode of action profiles. U.S. Pat. No. 3,177,252 discloses 4-aminobenzamides for the treatment of emesis, and behaviour disturbances. Metoclopramide belongs to the category of dopamine antagonists. EP 0 927 030 B1 embraces the use of declopramide (CAS No. 891-60-1) for inhibiting or killing tumour or cancer cells. Declopramide was listed amongst a number of small molecule NFκB inhibitors as a potential therapeutic agent for the treatment of autoimmune diseases, including IBD (Ivanenkov, 2011). Combined 5-ASA and procainamide were used in an attempt to improve the anticolitis efficacy of 5-ASA. Rectal administration of combined 5-ASA and procainamide elicited an additive anticolitis effect in the 2,4,6-trinitrobenzenesulfonic acid-induced rat colitis model (Kim, 2016). Neither rectal administration of combined 5-ASA and procainamide nor oral administration of 5-ASA azo-bonded to procainamide (5-ASA-azo-PA) did show superiority to oral SASP alone.

The well-known risk of potentially serious neurological and cardiovascular adverse events and the formation of antinuclear antibodies may outweigh potential clinical benefits of using 4-aminobenzamides in long-term treatment (Harrington, 1983; Harron, 1990).

4-Alkanoylaminobenzamides

U.S. Pat. No. 3,177,252 discloses 4-alkanoylaminobenzamides for the treatment of emesis, and behaviour disturbances. WO 99/63987 discloses 4-acetamido-3-chloro-N-[2-(diethylamino)ethyl]benzamide (N-acetyldeclopramide; hereinafter Cpd A) and uses thereof for inhibiting or killing tumour or cancer cells and as a potential therapeutic agent for treating inflammatory disorders. N-Acetylprocainamide (acecainide, CAS No. 32795-44-1) has been used for the treatment or prevention of cardiac arrhythmias.

The 4-aminobenzamides are known to inhibit NFκB, and these compounds were also found to induce apoptosis (Liberg, 1999). Acetylation of declopramide, giving Cpd A, obliterates the induction of apoptosis (Liberg 1999; Lindgren 2003), notwithstanding, markedly enhancing the NFκB inhibition compared to the corresponding 4-aminobenzamide (Liberg, 1999; Lindgren, 2001). While 4-aminobenzamides inhibit IκBα breakdown and the NFκB rescue pathway, the 4-alkanoylaminobenzamide analogues inhibit IκBβ breakdown and do not affect the NFκB rescue pathway (Lindgren, 2003).

SUMMARY OF THE INVENTION

One aspect is a compound of formula (I)

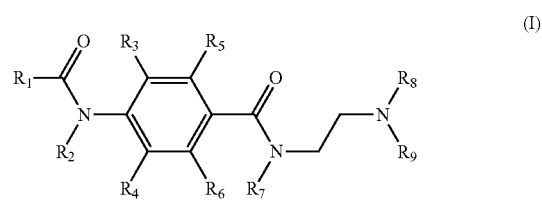

or a pharmaceutically acceptable salt or solvate thereof; wherein $R_1$ is selected from C1-C6 alkyl and C3-C6 cycloalkyl;

$R_2$ is selected from H and C1-C3 alkyl;

$R_3$, $R_4$, $R_5$, and $R_6$ are independently selected from hydrogen, C1-C3 alkyl, C1-C3 alkoxy, C1-C3 alkylthio, halogen, phenyl and benzyl, wherein any alkyl is optionally substituted with one or more fluoro;

$R_7$ is selected from hydrogen and C1-C3 alkyl;

$R_8$ and $R_9$ are independently selected from C1-C6 alkyl, or $R_8$ and $R_9$ together with the nitrogen atom to which they are both attached form a moiety of formula (II)

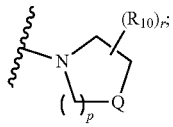

(II)

r is 0 or 1;
$R_{10}$ is selected from C1-C3 alkyl and C3-C4 cycloalkyl; said alkyl and cycloalkyl optionally being substituted with hydroxy, halogen, cyano, $COOR_{12}$, or $NHR_{13}$;
Q is selected from $CHR_{11}$, $NR_{11}$ and O;
$R_{11}$ is selected from hydrogen, C1-C3 alkyl and C3-C4 cycloalkyl; said alkyl and cycloalkyl optionally being substituted with hydroxy, halogen, cyano, $COOR_{12}$, or $NHR_{13}$;
$R_{12}$ and $R_{13}$ are independently selected from hydrogen, C1-C3 alkyl and C3-C4 cycloalkyl;
p is 1, 2, or 3 when Q is $CHR_{11}$; and
p is 2 or 3 when Q is selected from $NR_{11}$ and O;
for use in combination with a 5-ASA agent, in the treatment of a disease resulting from pathologic inflammation.

One aspect is a combination of:
(i) a compound of formula (I)

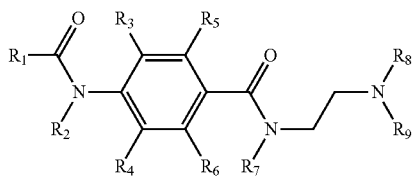

(I)

or a pharmaceutically acceptable salt or solvate thereof; wherein
$R_1$ is selected from C1-C6 alkyl and C3-C6 cycloalkyl;
$R_2$ is selected from H and C1-C3 alkyl;
$R_3$, $R_4$, $R_5$, and $R_6$ are independently selected from hydrogen, C1-C3 alkyl, C1-C3 alkoxy, C1-C3 alkylthio, halogen, phenyl and benzyl, wherein any alkyl is optionally substituted with one or more fluoro;
$R_7$ is selected from hydrogen and C1-C3 alkyl;
$R_8$ and $R_9$ are independently selected from C1-C6 alkyl, or
$R_8$ and $R_9$ together with the nitrogen atom to which they are both attached form a moiety of formula (II)

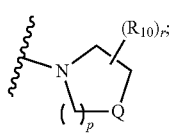

(II)

r is 0 or 1;
$R_{10}$ is selected from C1-C3 alkyl and C3-C4 cycloalkyl; said alkyl and cycloalkyl optionally being substituted with hydroxy, halogen, cyano, $COOR_{12}$, or $NHR_{13}$;
Q is selected from $CHR_{11}$, $NR_{11}$ and O;

$R_{11}$ is selected from hydrogen, C1-C3 alkyl and C3-C4 cycloalkyl; said alkyl and cycloalkyl optionally being substituted with hydroxy, halogen, cyano, $COOR_{12}$, or $NHR_{13}$;
$R_{12}$ and $R_{13}$ are independently selected from hydrogen, C1-C3 alkyl and C3-C4 cycloalkyl;
p is 1, 2, or 3 when Q is $CHR_{11}$; and
p is 2 or 3 when Q is selected from $NR_{11}$ and O; and
(ii) a 5-ASA agent.

A further aspect is a pharmaceutical composition comprising a combination as defined herein, and optionally a pharmaceutically acceptable excipient. The composition is useful for the treatment of pathologic inflammation, and in particular for the treatment of IBD.

A further aspect is a kit-of-parts comprising a combination as defined herein, wherein each one of components (i) and (ii) is optionally formulated in admixture with a pharmaceutically acceptable excipient. The kit-of-parts is useful for the treatment of pathologic inflammation, and in particular for the treatment of IBD.

Still a further aspect is the use of a compound of formula (I) as defined herein, or a salt or solvate thereof, in the manufacturing of a medicament for use in the treatment of a disease resulting from pathologic inflammation, wherein the treatment further comprises administration of a 5-ASA agent.

Still a further aspect is the use of a compound of formula (I) as defined herein, or a salt or solvate thereof, in the manufacturing of a medicament for use in the treatment of a disease resulting from pathologic inflammation, wherein the medicament further comprises a 5-ASA agent.

Still a further aspect is the use of a compound of formula (I), or a salt or solvate thereof, and of a 5-ASA agent in the manufacturing of a kit-of-parts for use in the treatment of pathologic inflammation, e.g. IBD.

A further aspect is a method for the treatment of a disease resulting from pathologic inflammation, comprising administering a therapeutically effective amount of a compound of formula (I), or a salt or solvate thereof, to a mammal in need of such treatment, in combination with administration of a 5-ASA agent to the mammal.

Other features and advantages of the invention will be understood by references to the detailed description and examples that follow.

DETAILED DESCRIPTION OF THE INVENTION

Definitions

As used herein, and unless stated otherwise or otherwise apparent from the context, each of the following terms shall have the definition set forth below.

The term "Cn alkyl" refers to a linear or branched chain saturated hydrocarbyl radical containing n carbon atoms in the chain, i.e. a moiety of formula $C_nH_{2n+1}$.

The term "Cn-Cm alkyl" refers to a linear or branched chain alkyl radical containing a number of carbon atoms in the chain ranging from n to m, wherein n and m are both integers and m is higher than n.

The term "Cn cycloalkyl" refers to a cyclic hydrocarbyl radical of formula $C_nH_{2n-1}$.

The term "Cn-Cm cycloalkyl" refers to a cyclic hydrocarbyl radical containing a number of carbon atoms in the cycle ranging from n to m, wherein n and m are both integers and m is higher than n.

The term "Cn-Cm alkoxy" refers to a moiety of formula

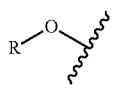

wherein R is Cn-Cm alkyl. For example, methoxy is C1 alkoxy.

The term "Cn-Cm alkylthio" refers to a moiety of formula

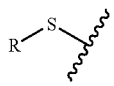

wherein R is Cn-Cm alkyl. For example, methylthio is C1 alkylthio.

The term "halogen" refers to F, Cl, Br or I; preferably F, Cl or Br.

The term "hydroxy" refers to the moiety

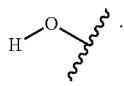

The term "phenyl" refers to a radical of formula

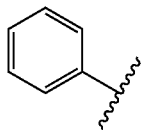

The term "benzyl" refers to a radical of formula

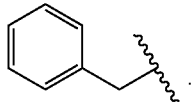

As used herein, "AABZ" means a compound of formula (I) as described herein. Unless otherwise indicated or apparent from the context, the term also includes a pharmaceutically acceptable salt or solvate (including hydrate) thereof.

As used herein, "about" in the context of a numerical value or range means±20% of the numerical value or range recited or claimed.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time.

As used herein, "administration", "administering" etc. means the giving of, dispensing of, or application of medicines, drugs, or remedies to a subject (e.g. a mammal subject, preferably a human) to relieve or cure a pathological condition. Oral administration is one way of administering the instant compounds to the subject.

As used herein, an "amount" or "dose" of a compound (e.g. AABZ) as measured in milligrams refers to the milligrams of the compound present in a preparation, regardless of the form of the preparation. A "dose of 5.0 mg of a compound" means the amount of compound in a preparation is 5.0 mg, regardless of the form of the preparation. Thus, when in the form of a salt, e.g. a hydrochloride, the weight of the salt form necessary to provide a dose of 5.0 mg of the free base compound would be greater than 5.0 mg due to the presence of the additional acid. As used herein, the term "5-ASA agent" means a compound containing the 5-aminosalicylic acid moiety. As used herein, the term also includes a salt or solvate of the compound, unless otherwise specified or apparent from the context.

As used herein, "combination" means an assemblage of compounds for use in therapy either by simultaneous or separate (e.g. sequential or concomitant) administration. Simultaneous administration refers to administration of an admixture (whether a true mixture, a suspension, an emulsion or other physical combination) of two active ingredients (e.g. the AABZ and the 5-ASA agent). In this case, the combination may be an admixture of the AABZ and the 5-ASA agent; or the AABZ and the 5-ASA agent may be provided in separate containers and combined just prior to administration. Separate administration may be sequential (i.e. consecutive) or concomitant (i.e. happening at the same time).

Separate administration refers to the concomitant or sequential administration of the AABZ and the 5-ASA agent as separate formulations, but at the same time or at times sufficiently close together for an activity to be observed that is at least additive, relative to the activity of either one of the AABZ and the 5-ASA agent alone.

As used herein, "CD" means Crohn's disease.

As used herein, "Cpd A" means 4-acetamido-3-chloro-N-[2-(diethylamino)ethyl]benzamide (N-acetyldeclopramide) hydochloride.

As used herein, "DSS" means Dextran Sulfate Sodium.

As used herein, "effective" when referring to an amount of an AABZ or of a 5-ASA agent refers to the amount that is sufficient to yield a desired therapeutic response without undue adverse side effects (such as toxicity, irritation, or allergic response), commensurate with a reasonable benefit/risk ratio when used in the manner of this invention.

As used herein, "excipient" is a substance formulated alongside the active ingredient of a medication included for such purposes as long-term stabilization, to provide bulk to a solid formulation, to act as a carrier and/or diluent, to confer a therapeutic enhancement on the active ingredient in the final dosage form, e.g. by facilitating absorption, reducing viscosity, or enhancing solubility. An excipient can also be useful in the manufacturing process, e.g. by facilitating powder flowability or providing non-stick properties. Examples of excipients are antiadherents, binders, coatings, colours, disintegrants, flavours, glidants, lubricants, preservatives, sorbents, sweeteners, and vehicles (carriers).

As used herein, "a disease resulting from pathologic inflammation" refers to diseases such as inflammatory bowel disease, rheumatic diseases, autoimmune diseases and disorders, and further, such diseases where inflammation plays a major role such as Alzheimer's disease, atherosclerosis and stroke. More particularly, as used herein, "a disease resulting from pathologic inflammation" refers to diseases and disorders selected from the group consisting of ulcerative colitis, Crohn's disease, rheumatoid arthritis, psoriatic arthritis, systemic lupus erythematosus, ankylosing spondylitis, psoriasis, multiple sclerosis, and type I diabetes, and in particular to diseases selected from the group consisting of ulcerative colitis and Crohn's disease.

As used herein, "IBD" means inflammatory bowel disease.

As used herein, "inhibition" of disease progression or disease complication in a subject means preventing or reducing the disease progression and/or disease complication in the subject.

As used herein, "NFκB" means nuclear factor kappa B.

As used herein "IκB" means inhibitor of kappa B.

As used herein, "pharmaceutically acceptable" refers to that which is suitable for use with humans and/or animals, generally safe and non-toxic at normal use, i.e. without undue adverse side effects (such as toxicity, irritation, and allergic response) commensurate with a reasonable benefit/risk ratio.

As used herein, "SASP" means sulfasalazine.

As used herein, a "salt thereof" is a salt of the instant compounds which have been modified by making acid or base salts of the compounds. The term "pharmaceutically acceptable salt" in this respect, refers to the relatively non-toxic, inorganic and organic acid or base addition salts of compounds of the present invention. For example, one means of preparing such a salt is by treating a compound of the present invention with an inorganic acid.

As used herein, a "solvate" means a physical association of a compound (e.g. a compound of formula (I)) with one or more solvent molecules, e.g. by hydrogen bonding. "Solvate" encompasses both solution-phase and isolable solvates. Exemplary solvates include, but are not limited to, hydrates, ethanolates, methanolates, and isopropanolates. Methods of solvation are generally known to the person of ordinary skill in the art.

As used herein, a "subject afflicted with a disease resulting from pathologic inflammation" means a subject who was been clinically diagnosed to have such a disease.

As used herein, a "symptom" associated with a disease resulting from pathologic inflammation includes any clinical or laboratory manifestation associated with the disease and is not limited to what the subject can feel or observe.

As used herein, "TF" means transcription factor.

As used herein, "TNF" means tumour necrosis factor.

As used herein, "TNF-α" means tumour necrosis factor alpha.

As used herein, "treating" encompasses, e.g., inducing inhibition, regression, or stasis of a disease or disorder, e.g., IBD, or alleviating, lessening, suppressing, inhibiting, reducing the severity of, eliminating or substantially eliminating, or ameliorating a symptom of the disease or disorder.

As used herein, "UC" means ulcerative colitis.

The IBDs including UC and CD are chronic, relapsing, and remitting conditions without a definitive cure. Current medications are moderately efficacious for induction and maintenance of clinical and endoscopic remission, and adverse effects are a problem. Thus, not all IBD patients respond adequately to currently available disease-modifying drugs.

An important objective of the present invention is to provide a new medicament and method for the treatment of a disease resulting from pathologic inflammation, e.g. IBD, with the final aim of changing the disease course. Without wishing to be bound to any theory, the present inventors have concluded that a more effective treatment of e.g. such diseases involves not just NFκB inhibition, but the use of NFκB inhibitors that in combination are capable of exerting a dual action on the NFκB activity. By combining NFκB inhibitors that together simultaneously inhibit the degradation of the two major forms of the IκB proteins, i.e., IκBα and IκBβ, a treatment superior to the existing therapy with 5-ASA alone is attainable. The inventors unexpectedly and surprisingly found that combining a compound of formula (I) with a greater than minimal effective amount of a 5-ASA agent as defined herein above results in a synergistically enhanced therapeutic effect, with a favourable safety profile.

Therefore, one further aspect is an AABZ for use in combination with a 5-ASA agent, in the treatment of a disorder (a disease resulting from pathologic inflammation, e.g. IBD), which disorder is associated with (e.g. mediated by) NFκB activity. A further aspect is an AABZ for use in combination with a 5-ASA agent, to inhibit NFκB activity in a mammalian (e.g. human) cell, for the treatment of a disorder (a disease resulting from pathologic inflammation, e.g. IBD) associated with (e.g. mediated by) NFκB activity. A further aspect is an AABZ, for use in combination with a 5-ASA agent, to inhibit the degradation of IκBα and IκBβ in a cell, for the treatment of a disorder (a disease resulting from pathologic inflammation, e.g. IBD) associated with (e.g. mediated by) NFκB activity in the cell. A further aspect is a method for the treatment of a disorder (a disease resulting from pathologic inflammation, e.g. IBD associated with (e.g. mediated by) NFκB activity, comprising administering a therapeutically effective amount of an AABZ in combination with a therapeutically effective amount of a 5-ASA agent, to a mammal in need of such treatment.

The Compound of Formula (I)

In a compound of formula (I) as defined herein, $R_1$ is selected from C1-C6 alkyl and C3-C6 cycloalkyl. In some embodiments, $R_1$ is selected from C1-C5 alkyl and C3-C5 cycloalkyl, e.g. from C1-C4 alkyl and C3-C4 cycloalkyl, or from C1-C3 alkyl and C3 cycloalkyl. In some embodiments, $R_1$ is selected from C1-C6 alkyl, e.g. from C1-C5 alkyl or from C1-C4 alkyl or from C1-C3 alkyl, or from C1-C2 alkyl. In some embodiments, $R_1$ is selected from methyl, ethyl, n-propyl, iso-propyl, cyclopropyl, n-butyl, sec-butyl, iso-butyl, tert-butyl, cyclobutyl, n-pentyl, sec-pentyl, iso-pentyl, tert-pentyl, neo-pentyl, and cyclopentyl; e.g. from methyl, ethyl, n-propyl, iso-propyl, cyclopropyl, n-butyl, sec-butyl, iso-butyl, tert-butyl, n-pentyl, sec-pentyl, iso-pentyl, tert-pentyl, and neo-pentyl. In some embodiments, $R_1$ is selected from methyl, ethyl, n-propyl, iso-propyl, cyclopropyl, n-butyl, sec-butyl, iso-butyl, tert-butyl, and cyclobutyl, e.g. from methyl, ethyl, n-propyl, iso-propyl, cyclopropyl, n-butyl, sec-butyl, iso-butyl, and tert-butyl. In some embodiments, $R_1$ is selected from methyl, ethyl, n-propyl, iso-propyl, and cyclopropyl, e.g. from methyl, ethyl, n-propyl, and iso-propyl. In some embodiments, $R_1$ is selected from methyl, ethyl, n-propyl, iso-propyl, n-butyl, sec-butyl, iso-butyl, tert-butyl, n-pentyl, sec-pentyl, iso-pentyl, tert-pentyl, and neo-pentyl; e.g. from methyl, ethyl, n-propyl, iso-propyl, n-butyl, sec-butyl, iso-butyl, and tert-butyl; or from methyl, ethyl, n-propyl, and iso-propyl; e.g. from methyl, ethyl, and iso-propyl. In some embodiments, $R_1$ is methyl or ethyl. In some embodiments, $R_1$ is methyl. In some embodiments, $R_1$ is ethyl. In some embodiments, $R_1$ is iso-propyl.

The moiety $R_2$ is selected from hydrogen and C1-C3 alkyl. In some embodiments, $R_2$ is selected from hydrogen, methyl, ethyl, n-propyl and iso-propyl; e.g. from hydrogen, methyl and ethyl; or from hydrogen and methyl. In some embodiments, $R_2$ is hydrogen.

The moieties $R_3$, $R_4$, $R_5$, and $R_6$ are independently selected from hydrogen, C1-C3 alkyl, C1-C3 alkoxy, C1-C3 alkylthio, halogen, phenyl and benzyl, wherein any alkyl is optionally substituted with one or more fluoro.

In some embodiments, $R_3$, $R_4$, $R_5$, and $R_6$ are independently selected from hydrogen, C1-C3 alkyl, C1-C3 alkoxy, C1-C3 alkylthio, and halogen, wherein any alkyl is optionally substituted with one or more fluoro. In some embodiments, $R_3$, $R_4$, $R_5$, and $R_6$ are independently selected from hydrogen, C1-C3 alkyl, C1-C3 alkoxy, and halogen, wherein any alkyl is optionally substituted with one or more fluoro. In still other embodiments, $R_3$, $R_4$, $R_5$, and $R_6$ are independently selected from hydrogen, C1-C3 alkyl, C1-C3 alkoxy, and halogen, wherein any alkyl is optionally substituted with one or more fluoro. In still other embodiments, $R_3$, $R_4$, $R_5$, and $R_6$ are independently selected from hydrogen, C1-C3 alkyl and halogen, wherein any alkyl is optionally substituted with one or more fluoro. In still other embodiments, $R_3$, $R_4$, $R_5$, and $R_6$ are independently selected from hydrogen, C1-C3 alkoxy and halogen, wherein any alkyl is optionally substituted with one or more fluoro. In still other embodiments, $R_3$, $R_4$, $R_5$, and $R_6$ are independently selected from hydrogen, C1-C3 alkoxy, C1-C3 alkylthio, and halogen, wherein any alkyl is optionally substituted with one or more fluoro. In still further embodiments, $R_3$, $R_4$, $R_5$, and $R_6$ are independently selected from hydrogen and halogen.

When any one of $R_3$, $R_4$, $R_5$, and $R_6$ is selected from C1-C3 alkyl, it e.g. may be selected from methyl and ethyl; in particular it may be methyl.

When any one of $R_3$, $R_4$, $R_5$, and $R_6$ is selected from C1-C3 alkoxy, it e.g. may be selected from methoxy and ethoxy; in particular it may be methoxy.

When any one of $R_3$, $R_4$, $R_5$, and $R_6$ is selected from C1-C3 alkylthio, it e.g. may be selected from methylthio and ethylthio; in particular it may be methylthio.

When any one of $R_3$, $R_4$, $R_5$, and $R_6$ is selected from halogen, said halogen e.g. may be selected from fluoro, chloro and bromo; in particular said halogen may be chloro or bromo, e.g. chloro. In some further embodiments, when any one of $R_3$, $R_4$, $R_5$, and $R_6$ is selected from halogen, said halogen more particularly is selected from fluoro and chloro.

In some embodiments, $R_3$, $R_4$, $R_5$, and $R_6$ are independently selected from hydrogen, methyl, ethyl, methoxy, ethoxy, methylthio, fluoro, chloro, bromo, trifluoromethyl, phenyl and benzyl, e.g. from hydrogen, methyl, ethyl, methoxy, ethoxy, methylthio, fluoro, chloro, bromo, and trifluoromethyl; or from hydrogen, methyl, ethyl, methoxy, ethoxy, fluoro, chloro, bromo, and trifluoromethyl; e.g. from hydrogen, methyl, methoxy, fluoro, chloro, bromo, and trifluoromethyl; or from hydrogen, methyl, methoxy, chloro, and trifluoromethyl, or from hydrogen, methyl, methoxy and chloro; or from hydrogen, methoxy and chloro; or from hydrogen, methyl and chloro; e.g. from hydrogen and chloro.

In some of the above embodiments, at least one, more preferably at least two of $R_3$, $R_4$, $R_5$, and $R_6$ are hydrogen. In some of the above embodiments, two of $R_3$, $R_4$, $R_5$, and $R_6$ are hydrogen. In some of the above embodiments, three of $R_3$, $R_4$, $R_5$, and $R_6$ are hydrogen. In some of the above embodiments, each one of $R_3$, $R_4$, $R_5$, and $R_6$ is hydrogen. In some of the above embodiments, at least one of $R_3$, $R_4$, $R_5$, and $R_6$ is different from hydrogen. In some of the above embodiments, one of $R_3$, $R_4$, $R_5$, and $R_6$ is different from hydrogen and the three others are hydrogen; e.g. one of $R_3$, $R_4$, $R_5$, and $R_6$ (e.g. $R_3$) is halogen, such as chloro; and the three others are hydrogen. In some of the above embodiments, $R_3$ is different from hydrogen, and each one of $R_4$, $R_5$, and $R_6$ is hydrogen. In some embodiments, $R_5$ is different from hydrogen, and each one of $R_3$, $R_4$, and $R_6$ is hydrogen. In some embodiments, one of $R_3$, $R_4$, $R_5$, and $R_6$ (e.g. $R_3$) is fluoro, chloro, or bromo, in particular chloro; and the three others are hydrogen. In some embodiments, $R_3$ is hydrogen or halogen, hydrogen and chloro; and $R_4$, $R_5$, and $R_6$ are hydrogen. In some embodiments, $R_4$, and $R_6$ are hydrogen; e.g. $R_4$ and $R_6$ are hydrogen and at least one of $R_3$ and $R_5$ is different from hydrogen, e.g. both $R_3$ and $R_5$ are different from hydrogen. In some embodiments, $R_4$ and $R_5$ are hydrogen; e.g. $R_4$ and $R_5$ are hydrogen and at least one of $R_3$ and $R_6$ is different from hydrogen, e.g. both $R_3$ and $R_6$ are different from hydrogen.

In some embodiments, $R_3$ and $R_4$ are hydrogen; e.g. $R_3$ and $R_4$ are hydrogen and at least one of $R_5$ and $R_6$ is different from hydrogen, e.g. both $R_5$ and $R_6$ are different from hydrogen. In some of the above embodiments, $R_5$ and $R_6$ are not methoxy or ethoxy.

The moiety $R_7$ is selected from hydrogen and C1-C3 alkyl. In some embodiments, $R_7$ is selected from hydrogen, methyl, ethyl, propyl and iso-propyl; e.g. from hydrogen, methyl, ethyl, and propyl. In some embodiments, $R_7$ is selected from hydrogen, methyl, and ethyl. In some embodiments, $R_7$ is selected from hydrogen and methyl. In some embodiments, $R_7$ is hydrogen.

The moieties $R_8$ and $R_9$ are independently selected from C1-C6 alkyl, or $R_8$ and $R_9$ together with the nitrogen atom to which they are both attach form a moiety of formula (II) as defined herein. In some embodiments, $R_8$ and $R_9$ are independently selected from C1-C6 alkyl. When $R_8$ and $R_9$ are selected from C1-C6 alkyl, $R_8$ and $R_9$ for example may be selected from C1-C5 alkyl; or from C1-C4 alkyl; or from C1-C3 alkyl; e.g. from methyl and ethyl. In some embodiments, when $R_8$ and $R_9$ are selected from C1-C6 alkyl, both $R_8$ and $R_9$ are ethyl. In some embodiments, $R_8$ and $R_9$ together with the nitrogen atom to which they are both attached form a moiety of formula (II) as defined herein, in which case the compound of formula (I) may be represented by formula (Ia)

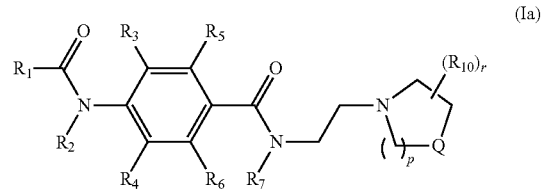

(Ia)

wherein $R_1$-$R_7$, $R_{10}$, Q, p and r are as defined herein.

In a moiety of formula (II), r is 0 or 1. In some embodiments, r is 0. In some embodiments, r is 1.

The moiety $R_{10}$ is selected from C1-C3 alkyl and C3-C4 cycloalkyl; said alkyl and cycloalkyl optionally being substituted with hydroxy, halogen, cyano, $COOR_{12}$, or $NHR_{13}$. In some embodiments, $R_{10}$ is selected from methyl, ethyl and cyclopropyl, said methyl, ethyl and cyclopropyl optionally being substituted with hydroxy, halogen, cyano, $COOR_{12}$, or $NHR_{13}$. In some embodiments, $R_{10}$ is selected from C1-C3 alkyl and C3-C4 cycloalkyl optionally substituted with hydroxy, halogen, and cyano; e.g. with halogen, such as fluoro. In some embodiments, $R_{10}$ is selected from C1-C3 alkyl and C3-C4 cycloalkyl, e.g. methyl, ethyl, and cyclopropyl, e.g. methyl.

The moiety Q is selected from $CHR_{11}$, $NR_{11}$ and O. In some embodiments, Q is selected from $CHR_{11}$ and $NR_{11}$. In some embodiments, Q is selected from $CHR_{11}$ and O. In some embodiments, Q is $CHR_{11}$. In some other embodiments, Q is selected from $NR_{11}$ and O.

The moiety $R_{11}$ is selected from hydrogen, C1-C3 alkyl and C3-C4 cycloalkyl; said alkyl and cycloalkyl optionally being substituted with hydroxy, halogen, cyano, COOR$_{12}$, or NHR$_{13}$. In some embodiments, $R_{11}$ is selected from hydrogen, methyl, ethyl and cyclopropyl, said methyl, ethyl and cyclopropyl optionally being substituted with hydroxy, halogen, cyano, COOR$_{12}$, or NHR$_{13}$. In some embodiments, $R_{11}$ is selected from hydrogen, C1-C3 alkyl and C3-C4 cycloalkyl, said alkyl and cycloalkyl optionally being substituted with hydroxy, halogen, or cyano; e.g. halogen, such as fluoro. In some embodiments, $R_{11}$ is selected hydrogen, C1-C3 alkyl and C3-C4 cycloalkyl, e.g. hydrogen, methyl, ethyl, and cyclopropyl, or hydrogen, methyl and ethyl; in particular hydrogen and methyl. In some embodiments, $R_{11}$ is hydrogen. In some other embodiments, $R_{11}$ is as defined herein above, but is different from hydrogen.

When $R_{11}$ is C1-C3 alkyl or C3-C4 cycloalkyl substituted with hydroxy, halogen, cyano, COOR$_{12}$, or NHR$_{13}$, the number of such substituents may be one or more, e.g. 1-3, or 1-2, or 1.

The moiety $R_{12}$ is selected from hydrogen, C1-C3 alkyl and C3-C4 cycloalkyl. In some embodiments, $R_{12}$ is selected from hydrogen, methyl, ethyl, n-propyl, iso-propyl and cyclopropyl, e.g. from hydrogen, methyl, ethyl, n-propyl, and iso-propyl; or from hydrogen, methyl and ethyl, e.g. from hydrogen and methyl. In some embodiments, $R_{12}$ is selected from hydrogen, C1-C3 alkyl and C3-C4 cycloalkyl. In some embodiments, $R_{12}$ is selected from C1-C3 alkyl and C3-C4 cycloalkyl, e.g. from methyl, ethyl, n-propyl, iso-propyl and cyclopropyl; from methyl, ethyl, n-propyl, and iso-propyl; or from methyl and ethyl, e.g. $R_{12}$ is methyl. In some other embodiments, $R_{12}$ is hydrogen.

The moiety $R_{13}$ is selected from hydrogen, C1-C3 alkyl and C3-C4 cycloalkyl. In some embodiments, $R_{13}$ is selected from hydrogen, methyl, ethyl, n-propyl, iso-propyl and cyclopropyl, e.g. from hydrogen, methyl, ethyl, n-propyl, and iso-propyl; or from hydrogen, methyl and ethyl, e.g. from hydrogen and methyl. In some embodiments, $R_{13}$ is selected from hydrogen, C1-C3 alkyl and C3-C4 cycloalkyl. In some embodiments, $R_{13}$ is selected from C1-C3 alkyl and C3-C4 cycloalkyl, e.g. from methyl, ethyl, n-propyl, iso-propyl and cyclopropyl; from methyl, ethyl, n-propyl, and iso-propyl; or from methyl and ethyl, e.g. $R_{13}$ is methyl. In some other embodiments, $R_{13}$ is hydrogen.

In the moiety of formula (II), p is 1, 2, or 3 when Q is CHR$_{11}$; and p is 2 or 3 when Q is selected from NR$_{11}$ and O. In some embodiments, p is 2 or 3. In some embodiments, p is 2. In some embodiments, Q is CHR$_{11}$ and p is 1 or 2. In some embodiments, Q is CHR$_{11}$, and p is 2. In some other embodiments, Q is CHR$_{11}$, and p is 1.

In some embodiments of a compound of formula (I), $R_1$ is C1-C6 alkyl; $R_2$ is hydrogen; $R_7$ is hydrogen; $R_8$ and $R_9$ are independently selected from C1-C6 alkyl, or $R_8$ and $R_9$ together with the nitrogen atom to which they are both attached form a moiety of formula (II) as defined herein; $R_{10}$ is C1-C3 alkyl; Q is CHR$_{11}$; and $R_{11}$ is selected from hydrogen and C1-C3 alkyl.

In some embodiments, $R_1$ a C1-C6 alkyl; $R_2$ is hydrogen; $R_7$ is hydrogen; and $R_8$ and $R_9$ are independently selected from C1-C6 alkyl. In some of these embodiments, $R_1$, $R_8$ and $R_9$ are independently selected from C1-C3 alkyl.

In some further embodiments, $R_1$ is C1-C3 alkyl; $R_2$, $R_4$, $R_5$ and $R_7$ are hydrogen; and $R_8$ and $R_9$ are independently selected from C1-C3 alkyl. In some of these embodiments, $R_1$ is selected from methyl, ethyl and iso-propyl; and $R_8$ and $R_9$ are the same or different and selected from methyl, ethyl and n-propyl.

In some further embodiments, $R_1$ is selected from methyl, ethyl and iso-propyl; $R_2$, $R_4$, $R_5$, $R_6$, and $R_7$ are hydrogen; and $R_8$ and $R_9$ are the same or different and selected from methyl, ethyl and n-propyl.

In some embodiments, $R_2$ is selected from hydrogen and methyl; $R_3$, $R_4$, $R_5$, and $R_6$ are independently selected from hydrogen and chloro; $R_7$ is hydrogen; and $R_8$ and $R_9$ are the same or different and selected from methyl, ethyl and n-propyl.

In some embodiments, $R_1$ is selected from methyl, ethyl and iso-propyl; $R_2$ is hydrogen or methyl; $R_3$ is chloro or hydrogen; $R_4$, $R_5$, $R_6$, and $R_7$ are hydrogen; and $R_8$ and $R_9$ are the same or different and are selected from methyl, ethyl and n-propyl. In some further embodiments, $R_1$ is selected from methyl, ethyl and iso-propyl; $R_2$ is hydrogen or methyl; $R_3$ is chloro or hydrogen; $R_4$, $R_5$, $R_6$, and $R_7$ are hydrogen; and $R_8$ and $R_9$ are ethyl. In some other embodiments, $R_1$ is selected from methyl, ethyl and iso-propyl; $R_2$ is hydrogen; $R_3$ is chloro or hydrogen; $R_4$, $R_5$, $R_6$, and $R_7$ are hydrogen; and $R_8$ and $R_9$ are the same or different and are selected from methyl, ethyl and n-propyl.

In some embodiments, $R_1$ is selected from methyl, ethyl and iso-propyl; $R_2$ is hydrogen; $R_3$ is chloro; $R_4$, $R_5$, $R_6$, and $R_7$ are hydrogen; and $R_8$ and $R_9$ are the same or different and are selected from methyl, ethyl and n-propyl.

In some embodiments, the compound of formula (I) is selected from:
4-acetamido-3-chloro-N-[2-(diethylamino)ethyl]benzamide,
4-propanamido-3-chloro-N-[2-(diethylamino)ethyl]benzamide,
4-isobutanamido-3-chloro-N-[2-(diethylamino)ethyl]benzamide,
4-acetamido-N-[2-(diethylamino)ethyl]benzamide,
N-[2-(diethylamino)ethyl]-4-(propanamido)benzamide, and
N-[2-(diethylamino)ethyl]-4-(isobutanamido)benzamide.

In some embodiments, the compound of formula (I) is selected from
4-acetamido-3-chloro-N-[2-(diethylamino)ethyl]benzamide,
4-propanamido-3-chloro-N-[2-(diethylamino)ethyl]benzamide,
4-isobutanamido-3-chloro-N-[2-(diethylamino)ethyl]benzamide, and
4-acetamido-N-[2-(diethylamino)ethyl]benzamide.

In some embodiments, the compound of formula (I) is 4-acetamido-3-chloro-N-[2-(diethylamino)ethyl]benzamide. In some embodiments, the compound of formula (I) is 4-propanamido-3-chloro-N-[2-(diethylamino)ethyl]benzamide. In some embodiments, the compound of formula (I) is 4-isobutanamido-3-chloro-N-[2-(diethylamino)ethyl]benzamide. In some embodiments, the compound of formula (I) is 4-acetamido-N-[2-(diethylamino)ethyl]benzamide. In some embodiments, the compound of formula (I) is N-[2-(diethylamino)ethyl]-4-(propanamido)benzamide. In some embodiments, the compound of formula (I) is N-[2-(diethylamino)ethyl]-4-(isobutanamido)benzamide.

In some embodiments, the AABZ is a hydrochloride of a compound of formula (I), e.g. a hydrochloride of any of the above listed compounds of formula (I), e.g. the AABZ is 4-acetamido-3-chloro-N-[2-(diethylamino)ethyl]benzamide hydrochloride.

Structural formulas of some compounds mentioned herein are shown in Table 1.

TABLE 1

| | |
|---|---|
| 4-acetamido-3-chloro-N-[2-(diethylamino)ethyl]benzamide | 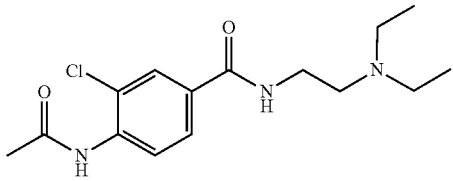 [SMILES: CCN(CC)CCNC(=O)c1ccc(NC(C)=O)c(Cl)c1] |
| 4-propanoylamino-3-chloro-N-[2-(diethylamino)ethyl]benzamide | 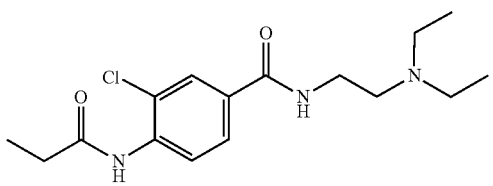 [SMILES: CCC(=O)Nc1ccc(C(=O)NCCN(CC)CC)cc1Cl] |
| 4-isobutyrylamino-3-chloro-N-[2-(diethylamino)ethyl]benzamide | 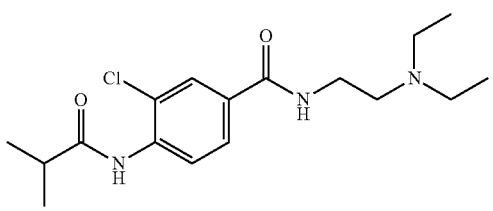 [SMILES: CCN(CC)CCNC(=O)c1ccc(NC(=O)C(C)C)c(Cl)c1] |
| 4-acetamido-N-[2-(diethylamino)ethyl]benzamide | 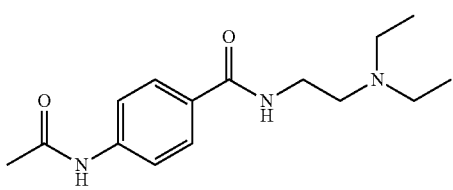 [SMILES: CCN(CC)CCNC(=O)c1ccc(NC(C)=O)cc1] |
| 4-propanoylamino-N-[2-(diethylamino)ethyl]benzamide | 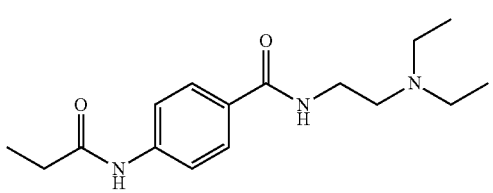 [SMILES: CCC(=O)Nc1ccc(C(=O)NCCN(CC)CC)cc1] |
| 4-isobutyrylamino-N-[2-(diethylamino)ethyl]benzamide | 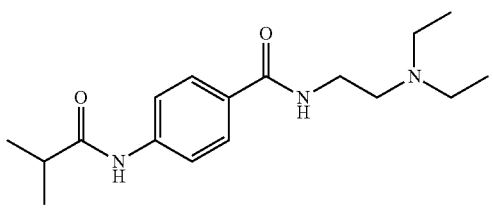 [SMILES: CCN(CC)CCNC(=O)c1ccc(NC(=O)C(C)C)cc1] |

Methods of Preparing the Compound of Formula (I)

The compounds of formula (I) may easily be prepared by the person of ordinary skill in the art, e.g. by following the general procedures as disclosed in US Patent Application No. 2011/0027179, and WO 2005/025498. For example, a compound of formula (I) may be prepared by a method comprising two consecutive nucleophilic substitution reactions as presented by the following reaction scheme.

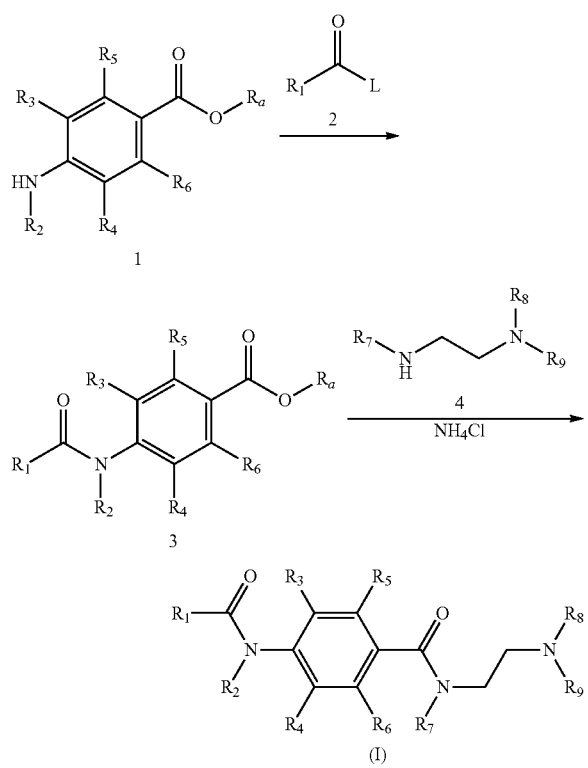

In the above reaction scheme, compound 1, where $R_a$ is e.g. C1-C3 alkyl, is reacted with compound 2, where L is a suitable leaving group, e.g. Cl, to obtain compound 3. Compound 3 is subsequently reacted with the secondary amine 4 in the presence of ammonium chloride as a catalyst for the reaction, to obtain the compound of formula (I) as defined herein. The compound of formula (I) may optionally be transformed to a suitable pharmaceutically acceptable salt or solvate, e.g. a hydrochloride salt.

The 5-ASA Agent

Examples of 5-ASA agents according to the invention are mesalazine, sulfasalazine, olsalazine or balsalazide (which may also be referred to as balsalazine), or pharmaceutically acceptable salts thereof. In Table 2, structural formulas of some 5-ASA agents are shown.

TABLE 2

| 5-ASA agent | Structural formula |
| --- | --- |
| mesalazine | |
| sulfasalazine | |
| olsalazine | |
| balsalazide | |

In some embodiments, the 5-ASA agent is mesalazine, sulfasalazine, olsalazine or balsalazide, or a pharmaceutically acceptable salt or solvate of any of these compounds. However, it should be noted that the invention is not limited to these compounds. Rather, any prodrug of 5-ASA or formulation capable of releasing 5-ASA or a salt or solvate thereof in vivo is contemplated as useful according to the invention.

In some embodiments, the 5-ASA agent is mesalazine or a pharmaceutically acceptable salt or solvate thereof. In some embodiments, the 5-ASA agent is sulfasalazine or a pharmaceutically acceptable salt or solvate thereof. In some embodiments, the 5-ASA agent is olsalazine or a pharmaceutically acceptable salt or solvate thereof. In some embodiments, the 5-ASA agent is balsalazide or a pharmaceutically acceptable salt or solvate thereof.

In some embodiments the 5-ASA agent is a colon-specific prodrug of 5-ASA designed to achieve colonic delivery. Such prodrugs comprise a carrier moiety attached to 5-ASA via the carboxylic or hydroxyl functional group of 5-ASA. As colon-specific prodrugs of 5-ASA, esters and amides have been reported (Amidon, 2015), and any such prodrug is contemplated as useful herein.

In particular, Amidon et al (2015) at page 731, describe criteria for colon specific drug delivery. In some embodiments, the 5-ASA agent is a colon-specific prodrug fulfilling such criteria for a colon-specific delivery.

Further examples of 5-ASA prodrugs useful herein are disclosed e.g. in U.S. Pat. No. 7,157,444 and in Jung (1998) and Jung (2003); e.g. 5-aminosalicyl-glycine and 5-aminosalicyl-taurine.

In some embodiments, the 5-ASA agent is a formulation capable of releasing 5-ASA or a salt or solvate thereof, or capable of releasing a 5-ASA prodrug, in vivo, e.g. in the colon. In some embodiments, the 5-ASA agent is a formulation capable of delayed release of 5-ASA or a salt thereof, e.g. a hydrochloride salt, in the colon.

The Pharmaceutically Acceptable Salts

The AABZ may be provided as a pharmaceutically acceptable salt of a compound of formula (I), e.g. an acid addition salt. Likewise, the 5-ASA agent may be provided as a pharmaceutically acceptable salt, e.g. a base addition salt. In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxy-maleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

In some embodiments the compound of formula (I) is provided as a hydrochloride. In some embodiments, the 5-ASA agent is provided as salt of a strong base, e.g. an alkali metal salt, such as a sodium salt.

Relevant teachings relating to salt formulations as used herein and processes for preparing the same are described, e.g., in U.S. Pat. No. 3,177,252, and such teachings are hereby incorporated by reference into this application.

The Pharmaceutically Acceptable Solvate

Any pharmaceutically acceptable solvate is contemplated as possible according to the present invention. Exemplary solvates include, but are not limited to, hydrates, ethanolates, methanolates, and isopropanolates. In some embodiments, the solvate is a hydrate.

The Combined Use of the AABZ and the 5-ASA Agent

One aspect is a compound of formula (I) as defined herein, or a pharmaceutically acceptable salt or solvate thereof (an AABZ), for use in combination with a 5-ASA agent, in the treatment of a disease resulting from pathologic inflammation.

In some embodiments, the treatment comprises administering to a subject (a mammal patient, e.g. a human patient) an amount of an AABZ, and a greater than minimal effective amount of a 5-ASA agent, wherein the amounts when taken together are effective to treat the subject. In some embodiments, the total amount of the AABZ and the 5-ASA agent when administered together to treat a subject produces an overall better effect, i.e., a synergistic effect, than the simple sum of effects produced when either component, at the same total amount, is administered alone.

In some embodiments, the treatment comprises administering to a subject (a mammal patient, e.g. a human patient) an AABZ as an add-on therapy or in combination with a 5-ASA agent in treating a subject afflicted with pathological inflammation, an IBD (e.g. UC or CD). Preferably, the treatment provides induction and maintenance of clinical and endoscopic remission in patients with mild to moderate to severe disease activity. In some embodiments, the treatment is intended for a patient in remission in order to prevent disease relapse.

In some embodiments, the AABZ is a pharmaceutically acceptable salt of a compound of formula (I), in particular a hydrochloride salt.

In some embodiments, the AABZ is administered via oral administration. In some embodiments, the AABZ is administered in a preferably solid unit formulation, which more preferably is a tablet.

In some embodiments, the amount of the AABZ administered is 0.1-25 mg/kg (mg of drug per kg of body weight of subject) per day (any weight value being based on the non-salt, non-solvate form). In other embodiments, the administered amount of the AABZ is 0.3-10 mg/kg per day.

In some embodiments, the amount of the AABZ administered is 5.0-2000 mg/day, or 10-1000 mg/day.

In some embodiment, the AABZ is administered daily, e.g. once daily. In other embodiments, the AABZ is administered twice daily. In other embodiments, the AABZ is administered three times daily. In yet other embodiments, the AABZ is administered four times daily.

In some embodiments, the 5-ASA agent is administered via oral administration. In yet other embodiments, the 5-ASA agent is administered via rectal administration.

In some embodiments, the 5-ASA agent is administered daily. In some embodiments, the amount of the 5-ASA agent administered is 250 mg/day to 8000 mg/day (any weight value being based on the non-salt, non-solvate form). In some embodiments, the amount of the 5-ASA agent administered is less than 8000 mg/day. In other embodiments, the amount of the 5-ASA agent administered is less than 6750 mg/day. In other embodiments, the amount of the 5-ASA agent administered is less than 4000 mg/day. In other embodiments, the amount of the 5-ASA agent administered is less than 2000 mg/day.

In some embodiments, the 5-ASA agent is administered once daily. In other embodiments, the 5-ASA agent is administered twice daily. In other embodiments, the 5-ASA agent is administered three times daily. In yet other embodiments, the 5-ASA agent is administered four times daily.

The amount of the AABZ and the amount of the 5-ASA agent when taken together preferably are effective to alleviate a symptom of pathologic inflammation, such as IBD, in the subject. Symptoms vary depending on the severity of inflammation and may range from mild to severe. Signs and symptoms that are common to both CD and UC include diarrhoea and urgency, fever and fatigue, abdominal pain and cramping, blood in the stool and reduced appetite. Symptoms of an autoimmune disease vary with the disease.

In some embodiments, the administration of the 5-ASA agent substantially precedes the administration of the AABZ, i.e. the subject is receiving therapy by administration of the 5-ASA agent prior to initiating therapy by administration of the AABZ.

In some embodiments, the subject is receiving therapy by administration of the 5-ASA agent for at least 6 months prior to initiating therapy by administration of the AABZ. In some embodiments, the subject is receiving therapy by administration of the 5-ASA agent for at least 12 months prior to initiating therapy by administration of the AABZ. In some embodiments, the subject is receiving therapy by administration of the 5-ASA agent for at least 24 months prior to initiating therapy by administration of the AABZ.

In some embodiments, the treatment comprises administration of at least one further drug, e.g. selected from nonsteroidal antiinflammatory drugs (NSAIDs), corticosteroids, cytotoxic drugs, immunosuppressive drugs and antibodies.

In some embodiments, the administration of the AABZ and the 5-ASA agent continues for at least 2 weeks. In other embodiments, the administration of the AABZ and the 5-ASA agent continues for 3 months or more. In yet other embodiments, the administration of the AABZ and the 5-ASA agent continues for 12 months or more.

In some embodiments, the AABZ and the 5-ASA agent are administered in combination with each other (simultaneously, or separately and concomitantly or sequentially) at the molar ratio of the AABZ to the 5-ASA ranging from 1:100 to 100:1, e.g. from 1:50 to 50:1, or from 1:20 to 20:1, or from 1:10 to 10:1, or from 1:5 to 5:1, or from 1:2 to 2:1, e.g. about 1:1.

In some embodiments, 4-acetamido-3-chloro-N-[2-(diethylamino)ethyl]benzamide or a pharmaceutically acceptable salt thereof, such as the hydrochloride salt, and sulfasalazine, or a or pharmaceutically acceptable salt thereof, such as a sodium salt, are administered in combination with each other.

The AABZ can be administered in admixture with suitable pharmaceutical diluents, extenders, or carriers, or any other pharmaceutically acceptable excipients, suitably selected with respect to the intended form of administration and as consistent with conventional pharmaceutical practices. A preferred dosage unit will be in a form suitable for oral administration. The AABZ can be administered alone but is generally mixed with a pharmaceutically acceptable carrier, and co-administered in the form of a tablet or capsule, liposome, or as an agglomerated powder. Examples of suitable solid carriers include lactose, sucrose, gelatine and agar. Capsule or tablets can be easily formulated and can be made easy to swallow or chew; other solid forms include granules, and bulk powders.

Tablets may contain suitable binders, lubricants, disintegrating agents, colouring agents, flavouring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatine, agar, starch, sucrose, glucose, methyl cellulose, dicalcium phosphate, calcium sulphate, mannitol, sorbitol, microcrystalline cellulose and the like. Suitable binders include starch, gelatine, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

A further aspect is an AABZ for use as an add-on therapy or in combination with a 5-ASA agent in treating a subject afflicted with pathologic inflammation such as IBD.

A further aspect is a 5-ASA agent for use in the treatment of a subject afflicted with pathologic inflammation such as IBD, by administering to the subject the 5-ASA agent and the AABZ.

The Treated Subject

The subject that is treated according to the present invention is a mammal, including a human and a non-human mammal (an animal). Examples, of non-human mammals are primates, domesticated animals, e.g. farm animals, e.g. cattle, sheep, pigs, horses and the like, as well as pet animals, such as dogs and cats, and the like. In preferred embodiments, the subject is a human. In some other embodiments, the subject is a non-human mammal, e.g. a dog or a horse.

The Disease

The disease treated according to the present invention is a disease resulting from pathologic inflammation, as defined herein. In some embodiments, the disease is IBD. In some embodiments, the disease is UC. In some embodiments, the disease is CD. As mentioned herein above, CD may affect any part of the gastrointestinal tract. In some embodiments, the CD is affecting the colon.

The Kit-of-Parts

One aspect is a kit-of-parts comprising a combination of an AABZ and a 5-ASA agent, wherein each one of components the AABZ and the 5-ASA agent is optionally formulated in admixture with a pharmaceutically acceptable excipient, such as a carrier. In some embodiments, a kit-of-parts is provided, comprising: a) a first pharmaceutical composition comprising an amount of an AABZ and a pharmaceutically acceptable carrier; b) a second pharmaceutical composition comprising an amount of a 5-ASA agent and a pharmaceutically acceptable carrier; and c) instructions for use of the first and the second pharmaceutical compositions together; e.g. for use in the treatment of IBD.

The Pharmaceutical Composition

One aspect is a pharmaceutical composition comprising an amount of an AABZ, an amount of a 5-ASA agent, and optionally (but preferably) at least one pharmaceutically acceptable excipient, such as a carrier. In some embodiments, the pharmaceutical composition is for use in treating a subject afflicted with IBD.

Generally, a suitable pharmaceutical composition is one as described herein above, in connection with a pharmaceutical formulation of an AABZ, but in addition to an AABZ, the composition also contains a 5-ASA agent.

In some embodiments, the AABZ is a pharmaceutically acceptable salt of a compound of formula (I), e.g. a hydrochloride.

In some embodiments, the amount of AABZ in the composition is 5-500 mg (any amount is based on the compound of formula (I) in non-salt form and non-solvated form). In other embodiments, the amount of AABZ is 10-100 mg. In other embodiments, the amount of AABZ is 5-25 mg. In one embodiment, the amount of AABZ in the composition is 500 mg. In other embodiments, the amount of AABZ is 25 mg. In other embodiments, the amount of AABZ is 100 mg. In other embodiments, the amount of AABZ is 10 mg. In other embodiments, the amount of AABZ is less than 10 mg.

In some embodiments, the amount of 5-ASA agent in the composition is 225-1200 mg (any amount is based on the compound of formula (I) in non-salt form and non-solvated form). In other embodiments, the amount of 5-ASA agent is 500-1000 mg. In other embodiments, the amount of 5-ASA agent is 225-450 mg. In one embodiment, the amount of 5-ASA agent in the composition is 750 mg.

In some embodiments, the molar ratio of the AABZ to the 5-ASA in the pharmaceutical composition ranges from 1:100 to 100:1, e.g. from 1:50 to 50:1, or from 1:20 to 20:1, or from 1:10 to 10:1, or from 1:5 to 5:1, or from 1:2 to 2:1, e.g. it may be about 1:1.

In some embodiments the total amount of the AABZ and the 5-ASA agent is between 0.1 and 95% by weight of the formulation, e.g. between 0.5 and 50% by weight, or between 1 and 20% by weight, the remainder comprising e.g. a carrier and any other excipient.

In some embodiments, the pharmaceutical composition comprises 4-acetamido-3-chloro-N-[2-(diethylamino)ethyl] benzamide or pharmaceutically acceptable salt thereof, such as the hydrochloride salt, and sulfasalazine, or a pharmaceutically acceptable salt thereof, such as a sodium salt.

Specific examples of the techniques, pharmaceutically acceptable carriers and excipients that may be used to formulate oral dosage forms of the present invention are described, e.g., in EP 1 720 531 B1. General techniques and compositions for making dosage forms useful in the present invention are described-in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985) (and subsequent editions); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds); and Modern Pharmaceutics Drugs and the Pharmaceutical Sciences, Vol. 40 (Gilbert S. Banker, Christopher T. Rhodes, Eds). These references in their entireties are hereby incorporated by reference into this application.

The following examples are intended to illustrate the invention without restricting the scope thereof.

EXAMPLES

Intermediary 1

Ethyl-4-acetamido-3-chlorobenzoate

Ethyl-4-amino-3-chlorobenzoate (2.0 g, 10 mmol) and 1.4 g of triethylamine were dissolved in 20 mL of dichloromethane. 0.9 g of acetyl chloride in 5 mL of dichloromethane was added drop-wise at 0° C. The reaction mixture was allowed to reach room temperature, stirred for 3 hours, washed with water, and dried. The solvents were evaporated to yield 2.0 g of the title product.

Example 1

4-Acetamido-3-chloro-N-[2-(diethylamino)ethyl] benzamide hydrochloride 1.5 g of ethyl-4-acetamido-3-chlorobenzoate (1.5 g, 6.2 mmol) was dissolved in 15 mL of N',N'-diethylethane-1,2-diamine together with a catalytic amount of ammonium chloride. The reaction mixture was refluxed for 3 hours. Dichloromethane was added and washing 4 times with water removed excess diamine. Drying and evaporation of the solvents yielded the free base of the title compound. The residue was dissolved in ethanol-ether and acidified with ethanolic HCl. The solid that precipitated was collected giving the title compound (1.1 g, 3.1 mmol, 50% yield). 1H NMR (DMSO-d6): δ 1.23 (t, 6H), 2.15 (s, 3H), 3.17-3.23 (6H), 3.65 (q, 2H), 7.88 (d, 1H), 7.94 (s, 1H), 8.06 (s, 1H), 9.05 (t, 1H), 9.68 (s, 1H), 10.42 (s, 1H).

Example 2

4-Propanamido-3-chloro-N-[2-(diethylamino)ethyl] benzamide hydrochloride

4-Amino-N-[2-(diethylamino)ethyl]benzamide hydrochloride (0.5 g, 1.6 mmol), pyridine (5.0 mL), and propionic anhydride (5.0 mL) were stirred at 50° C. for 2.5 hours. Then the volatiles were removed using a rotary evaporator. Water (5 mL) was added and evaporated. The residue was freeze dried from water and gave the title compound (0.6 g, 100% yield, HPLC purity 98%). 1H NMR (400 MHz, Methanol-d4) δ 8.07 (d, J=8.6 Hz, 1H), 8.01 (d, J=2.0 Hz, 1H), 7.83 (dd, J=8.6, 2.0 Hz, 1H), 3.76 (t, J=6.2 Hz, 2H), 3.39 (t, J=6.2 Hz, 2H), 3.34 (q, J=7.3 Hz, 4H), 2.52 (q, J=7.6 Hz, 2H), 1.36 (t, J=7.3 Hz, 6H), 1.23 (t, J=7.6 Hz, 3H).

Example 3

4-Isobutanamido-3-chloro-N-[2-(diethylamino)ethyl] benzamide hydrochloride

The compound 4-isobutanamido-3-chloro-N-[2-(diethylamino)ethyl]benzamide hydrochloride was obtained in essentially the same manner, by use of Isobutyric anhydride instead of propionic anhydride. Purity by HPLC 99%.

1H NMR (400 MHz, Methanol-d4) δ 8.01 (d, J=2.2 Hz, 1H), 8.00 (d, J=8.5 Hz, 1H), 7.83 (dd, J=8.5, 2.0 Hz, 1H), 3.76 (t, J=6.2 Hz, 2H), 3.39 (t, J=6.2 Hz, 2H), 3.34 (q, J=7.3 Hz, 4H), 2.80 (hept, J=6.8 Hz, 1H), 1.36 (t, J=7.3 Hz, 6H), 1.24 (d, J=6.9 Hz, 6H).

Example 4

4-Acetamido-N-[2-(diethylamino)ethyl]benzamide hydrochloride

A suspension of 4-amino-N-[2-(diethylamino)ethyl]benzamide hydrochloride (2.5 g, 9.1 mmol) was stirred in 20 mL of anhydrous pyridine. To the suspension was added 10 mL of acetic anhydride. The reaction was slightly exothermic. After 1 hour the precipitate was filtered off, washed with ethyl acetate, and dried to afford the title compound (2.83 g, 9.0 mmol, 99% yield). Purity by NMR 98%.

1H NMR (400 MHz, Methanol-d4) δ 7.84 (d, 2H), 7.68 (d, 2H), 3.74 (t, 2H), 3.37 (t, 2H), 3.35-3.29 (m, 4H), 2.14 (s, 3H), 1.35 (t, 6H).

Biological Assays

UC is an inflammatory disease characterized by the infiltration of inflammatory cells, such as macrophages, into the lesioned colon. Macrophages serve a critical role in the initiation and propagation of inflammatory responses by releasing proinflammatory mediators, such as TNF-α. Lipopolysaccharide (LPS) is a potent initiator of an inflammatory response. During LPS stimulation, NF-κB signaling is activated to regulate the transcription of numerous genes involved in immunity and inflammation to produce proinflammatory cytokines, such as TNF-α. Suppression of LPS-induced TNF-α production in RAW264.7 macrophages treated with AABZ was investigated by evaluation of the generation of TNF-α. The aim of this study was to evaluate the anti-inflammatory activity of AABZ.

Both dextran sulphate sodium (DSS) and trinitrobenzene sulfonic acid (TNBS) induced colitis are well-established animal models of mucosal inflammation that have been used for over 2 decades in the study of IBD pathogenesis and preclinical studies for new therapeutics. The DSS-induced colitis model has some advantages when compared to other animal models of colitis (Perse, 2012) and was therefore chosen for analysis of combination treatment effects.

Example 5

Suppression of LPS-Induced TNF-α Production in Macrophages Treated with AABZ.

The RAW264.7 macrophage line was maintained in DMEM supplemented with 5% FBS at 37° C. in a 5% 002-humidified air environment. The RAW264.7 cells were seeded in 96-well plates at a density of 1×105/ml and a volume of 200 μl/well. The cells were incubated for 24 h in medium supplemented with 10% FBS and were then preincubated with or without the indicated concentrations of test substances for 2 h prior to the addition of LPS (1 µg/ml). The supernatants were subsequently harvested at various time points and production of the proinflammatory cytokine TNF-α in the culture medium was determined using a commercially available enzyme-linked immunosorbent assay (ELISA) kit according to the manufacturer's protocol.

Effects of some AABZs of the invention at 1 mM on LPS-induced TNF-production in RAW264.7 murine macrophage cells are shown in Table 3.

TABLE 3

Effects of AABZs at 1 mM on LPS-induced TNF-production in RAW264.7 murine macrophage cells

| Compound | % Inhibition of TNF-production |
|---|---|
| LPS-treated control | 0 |
| 4-Acetamido-3-chloro-N-[2-(diethylamino)ethyl]benzamide hydrochloride* | 45 |
| 4-Propanamido-3-chloro-N-[2-(diethylamino)ethyl]benzamide hydrochloride | 50 |
| 4-Isobutanamido-3-chloro-N-[2-(diethylamino)ethyl]benzamide hydrochloride | 63 |
| 4-Acetamido-N-[2-(diethylamino)ethyl]benzamide hydrochloride | 56 |

*Cpd A

It was observed that different concentrations (0.3, 1.0, and 3.0 mM) of the compounds significantly reduced the expression levels of TNF in comparison with the LPS-treated control group. These results support the usefulness of compounds as disclosed herein, for the treatment of diseases resulting from pathologic inflammation.

solution (DSS from TdB Consultary AB, Sweden; MW~40000) for five days (day 0 to day 5) via the drinking water, which resulted in reproducible colitis characterized by diarrhoea, rectal bleeding, reduced body weight, mucosal ulceration, crypt destruction and infiltration of leukocytes. The DSS intake was assessed daily.

SASP (from Sigma-Aldrich, Sweden) was first dissolved in 0.2 M sodium hydroxide (NaOH) at a concentration higher than the required final concentration. Phosphate buffered saline (PBS) was added to the desired concentration and the pH was adjusted to 7.5-8.0 with NaOH or hydrochloric acid. SASP remained completely dissolved at this pH. Cpd A hydrochloride was dissolved in PBS to the desired concentration.

All animal groups had free access to 5% DSS water solution for the entire test period. Treatments were administered from day 0 to day 5, either orally by gavage (SASP) or intraperitoneally (Cpd A), and in an administration volume of 5 ml/kg, twice daily with approximately an 8-hour interval. The control group (DSS only) received water (0.2 ml) orally twice daily. The parameters recorded in the experiment were stool consistency (0, normal; 2, loose stools; 4, watery diarrhoea), occurrence of blood in the stool (0, normal; 2, Hemoccult+; 4, gross bleeding), and body weight loss (0, none; 1, 1-5%; 2, 5-10%; 3, 10-20%; 4, >20%). Disease activity index (DAI) was calculated by summarizing the scores of these three parameters. Also the colon length and the colonic content of myeloperoxidase (MPO) were recorded. Data was statistically evaluated with analysis of variance (ANOVA). Least-squares means (LS means), and standard error (SE) of LS means were calculated.

Table 4 shows the recorded percentage inhibition on day 5 of the dextran sulphate sodium effect (100%=complete normalisation, 0%=no effect).

TABLE 4

Percentage inhibition on day 5 of dextran sulphate sodium disease activity index (100% = complete normalisation, 0% = no effect) vs control.

| | | | | Disease Activity Index | | |
|---|---|---|---|---|---|---|
| AABZ | Dose mg/kg/day bid ip | 5-ASA Agent | Dose mg/kg/day bid po | LS means ± SE | p-value vs Control | Percent Reduction of Score |
| | | Control | | 6.9 ± 0.3 | | |
| | | SASP | 20 | 6.4 ± 0.5 | 0.34 | 8 |
| | | SASP | 40 | 4.4 ± 0.4 | <0.0001 | 36 |
| Cpd A | 50 | | | 6.4 ± 0.5 | 0.41 | 7 |
| Cpd A | 50 | SASP | 20 | 3.4 ± 0.7 | <0.0001 | 51 |

Example 6

Assessment of Efficacy of Cpd A Alone or in Combination with SASP in Dextran Sulfate Sodium (DSS)-Induced Inflammatory Bowel Disease The experiment was performed using 6-8-week-old female Balb/c mice after a one-week acclimatization period. The mice weighed 18-25 g, were purchased from Taconic (Denmark) and were maintained in a temperature and light-controlled facility with free access to standard rodent chow and water. Mice were randomized to the respective groups five days before start of treatment and were kept 5 to 6 animals per cage. Following the acclimatization period, acute colitis was induced by administration of 5% DSS Administration of 5% DSS for 5 days resulted in severe acute colitis, with diarrhoea, blood in faeces and weight loss. Diarrhoea and blood in faeces appeared from day 3 and these symptoms aggravated until study termination on day 5. Oral treatment with SASP (40 mg/kg/day bid was found to be the optimal dose) ameliorated some of these manifestations of colitis. There was an improvement of diarrhoea as well as blood in faeces from day 3 onwards. The frequency of diarrhoea (stool consistency score of 2 and 4) amounted to 22% in the control group and 8% in the SASP 40 mg/kg/day bid group on day 3. On day 5, the corresponding figures were 98% and 71%, respectively. Combination of Cpd A (50 mg/kg/day bid) with SASP (20 mg/kg/day bid) resulted in a superior amelioration of the colitis parameters (Table 4).

Cpd A combined with SASP acted synergistically (p<0.008) in ameliorating DSS-induced acute colitis. The Disease Activity Index (DAI) score was significantly reduced by the combination treatment by 51% versus the control group (p<0.0001) and by 47% versus the SASP (20 mg/kg/day bid) alone group (p<0.0002).

REFERENCES

Amidon S, et al. AAPS PharmSciTech. 2015 16:731-41.
Azad Khan A K, et al. Lancet. 1977 310:892-5.
Hanauer S B. Aliment Pharmacol Ther 2004 20:60-65.
Harrington R A, et al. Drugs 1983 25:451-94.
Harron D W G, et al. Drugs 1990 39: 720-740.
Ivanenkov Y A, et al. Mini Rev Med Chem. 2011 1:55-78.
Jung Y J, et al. Arch Pharm Res. 1998 21:174-8.
Jung Y J, et al. Arch Pharm Res. 2003 26:264-9.
Kaiser G C, et al. Gastroenterology. 1999 116:602-9.
Kim W, et al. Mol Pharm. 2016 13:2126-35.
Liberg D, et al. Br J Cancer. 1999 81:981-8.
Lim W C, et al. Cochrane Database Syst Rev. 2016 7:CD008870.
Lindgren H, et al. Mol Immunol. 2001 38:267-77.
Lindgren H, et al. Biochem Biophys Res Commun. 2003 301:204-11.
MacDermott R P. Am J Gastroenterol. 2000 95:3343-5.
Mills S, et al. Clin Colon Rectal Surg. 2007 20: 309-313.
Peppercorn M A, et al. J Pharmacol Exp Ther. 1972 181: 555-62.
Pero R W, et al. Cancer Detect Prev. 1998 22: 225-236.
Pero R W, et al. Mol. Cell. Biochem. 1999 193:119-125.
Pere M, et al. J Biomed Biotechnol. 2012 2012:718617.
Rang H P, et al. Br J Anaesth. 1995 75:145-56.
Stanley M, et al. 1982 The Benzamides: Pharmacology, Neurobiology and Clinical Aspects. Raven Press: New York.
Svartz N. Acta Medica Scandinavica. 1942 110:577-598.
Thompson J E, et al. Cell. 1995 80:573-82.
van Hees P A, et al. Gut. 1980 21:632-5.
Wahl C, et al. J Clin Invest. 1998 101:1163-74.
Wang Y, et al. Cochrane Database Syst Rev. 2016a 4:CD000543.
Wang Y, et al. Cochrane Database Syst Rev. 2016b 5:CD000544.
Zhao W, et al. Yakugaku Zasshi. 2010 130:1239-49.

The invention claimed is:

1. A method for the treatment of a disease resulting from pathologic inflammation, comprising administering a therapeutically effective amount of a compound of formula (I)

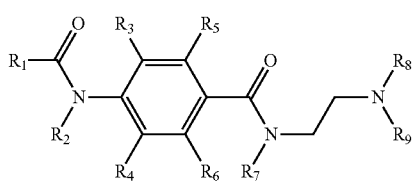

or a pharmaceutically acceptable salt or solvate thereof; wherein
$R_1$ is selected from C1-C6 alkyl and C3-C6 cycloalkyl;
$R_2$ is selected from H and C1-C3 alkyl;
$R_3$, $R_4$, $R_5$, and $R_6$ are independently selected from hydrogen, C1-C3 alkyl, C1-C3 alkoxy, C1-C3 alkylthio, and halogen, wherein any alkyl is optionally substituted with one or more fluoro;
$R_7$ is selected from hydrogen and C1-C3 alkyl; and
$R_8$ and $R_9$ are independently selected from C1-C6 alkyl;
wherein the treatment also includes administration of a 5-ASA agent selected from mesalazine, sulfasalazine, olsalazine, and balsalazide or a pharmaceutically acceptable salt or solvate thereof.

2. The method according to claim 1, wherein
$R_3$, $R_4$, $R_5$, and $R_6$ are independently selected from hydrogen, C1-C2 alkyl, C1-C2 alkoxy, C1-C2 alkylthio, halogen, and trifluoromethyl;
$R_7$ is selected from hydrogen and C1-C3 alkyl; and
$R_8$ and $R_9$ are independently selected from C1-C6 alkyl or a pharmaceutically acceptable salt or solvate thereof.

3. The method according to claim 1, wherein at least two of $R_3$, $R_4$, $R_5$, and $R_6$ are hydrogen.

4. The method according to claim 1, wherein
$R_1$ is selected from C1-C3 alkyl;
each one of $R_2$, $R_4$, $R_5$, $R_6$ and $R_7$ is hydrogen; and
$R_8$ and $R_9$ are independently selected from C1-C4 alkyl.

5. The method according to claim 1, wherein
the compound of formula (I) is selected from
4-acetamido-3-chloro-N-[2-(diethylamino)ethyl]benzamide,
4-propanamido-3-chloro-N-[2-(diethylamino)ethyl]benzamide,
4-isobutanamido-3-chloro-N-[2-(diethylamino)ethyl] benzamide,
4-acetamido-N-[2-(diethylamino)ethyl]benzamide,
N-[2-(diethylamino)ethyl]-4-(propanamido)benzamide, and
N-[2-(diethylamino)ethyl]-4-(isobutanamido)benzamide.

6. The method according to claim 5, wherein the compound of formula (I) is 4-acetamido-3-chloro-N-[2-(diethylamino)ethyl]benzamide.

7. The method according to claim 5, wherein the compound of formula (I) is 4-propanamido-3-chloro-N-[2-(diethylamino)ethyl]-benzamide.

8. The method according to claim 5, wherein the compound of formula (I) is 4-isobutanamido-3-chloro-N-[2-(diethylamino)ethyl]-benzamide.

9. The method according to claim 5, wherein the compound of formula (I) is 4-acetamido-N-[2-(diethylamino)ethyl]benzamide.

10. The method according to claim 1, wherein the disease is an inflammatory bowel disease.

11. The method according to claim 10, wherein the inflammatory bowel disease is ulcerative colitis.

12. The method according to claim 10, wherein the inflammatory bowel disease is Crohn's disease.

13. A combination of:
(i) a compound of formula (I)

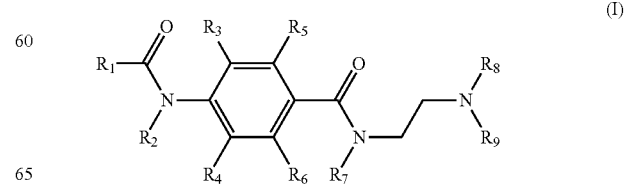

or a pharmaceutically acceptable salt or solvate thereof; wherein $R_1$ is selected from C1-C6 alkyl and C3-C6 cycloalkyl;

$R_2$ is selected from H and C1-C3 alkyl;

$R_3$, $R_4$, $R_5$, and $R_6$ are independently selected from hydrogen, C1-C3 alkyl, C1-C3 alkoxy, C1-C3 alkylthio, and halogen, wherein any alkyl is optionally substituted with one or more fluoro;

$R_7$ is selected from hydrogen and C1-C3 alkyl; and $R_8$ and $R_9$ are independently selected from C1-C6 alkyl; and (ii) a 5-ASA agent selected from mesalazine, sulfasalazine, olsalazine, and balsalazide or a pharmaceutically acceptable salt or solvate thereof.

14. The combination according to claim 13, wherein $R_3$, $R_4$, $R_5$, and $R_6$ are independently selected from hydrogen, C1-C2 alkyl, C1-C2 alkoxy, C1-C2 alkylthio, halogen, and trifluoromethyl;

$R_7$ is selected from hydrogen and C1-C3 alkyl; and $R_8$ and $R_9$ are independently selected from C1-C6 alkyl;

or a pharmaceutically acceptable salt or solvate thereof.

15. The combination according to claim 13, wherein at least two of $R_3$, $R_4$, $R_5$, and $R_6$ are hydrogen.

16. The combination according to claim 13, wherein $R_1$ is selected from C1-C3 alkyl;

each one of $R_2$, $R_4$, $R_5$, $R_6$ and $R_7$ is hydrogen; and $R_8$ and $R_9$ are independently selected from C1-C4 alkyl.

17. The combination according to claim 13, wherein the compound of formula (I) is selected from
    4-acetamido-3-chloro-N-[2-(diethylamino)ethyl]benzamide,
    4-propanamido-3-chloro-N-[2-(diethylamino)ethyl]benzamide,
    4-isobutanamido-3-chloro-N-[2-(diethylamino)ethyl]benzamide,
    4-acetamido-N-[2-(diethylamino)ethyl]benzamide,
    N-[2-(diethylamino)ethyl]-4-(propanamido)benzamide, and
    N-[2-(diethylamino)ethyl]-4-(isobutanamido)benzamide.

18. The combination according to claim 17, wherein the compound of formula (I) is 4-acetamido-3-chloro-N-[2-(diethylamino)ethyl]benzamide.

19. The combination according to claim 17, wherein the compound of formula (I) is 4-propanamido-3-chloro-N-[2-(diethylamino)ethyl]benzamide.

20. The combination according to claim 17, wherein the compound of formula (I) is 4-isobutanamido-3-chloro-N-[2-(diethylamino)ethyl]benzamide.

21. The combination according to claim 17, wherein the compound of formula (I) is 4-acetamido-N-[2-(diethylamino)ethyl]benzamide.

22. A pharmaceutical composition comprising a combination as defined in claim 13, and optionally a pharmaceutically acceptable excipient.

23. A kit-of-parts comprising a combination as defined in claim 13, wherein each one of components (i) and (ii) is optionally formulated in admixture with a pharmaceutically acceptable excipient.

* * * * *